US00PP32055P2

(12) United States Plant Patent
Lambert et al.

(10) Patent No.: US PP32,055 P2
(45) Date of Patent: Aug. 11, 2020

(54) ***HYDRANGEA* PLANT NAMED 'FRENCH BOLERO'**

(50) Latin Name: ***Hydrangea* hybrid**
Varietal Denomination: FRENCH BOLERO

(71) Applicant: SARL Hydrangea Worldwide, Sainte-Gemmes-sur-Loire (FR)

(72) Inventors: Claudie Lambert, Angers (FR); Helene Bertrand, Angers (FR)

(73) Assignee: SARL Hydrangea Worldwide (FR)

( * ) Notice: Subject to any disclaimer, the term of this patent is extended or adjusted under 35 U.S.C. 154(b) by 0 days.

(21) Appl. No.: 16/602,462

(22) Filed: Oct. 10, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Hydrangea* plant named 'FRENCH BOLERO' is disclosed, characterized by a distinct combination of small, narrow foliage, and a flattened lacecap inflorescence composed of light pink flowers. Plants are sterile, begin flowering early and produce numerous thin stems. The new variety is a *Hydrangea*, normally produced as an ornamental plant for containers or gardens.

2 Drawing Sheets

Latin name of the genus and species: *Hydrangea* hybrid. Variety denomination: 'FRENCH BOLERO'.

BACKGROUND OF THE INVENTION

The new *Hydrangea* cultivar is a product of a planned breeding program conducted by the inventors, Claudie Lambert and Helene Bertrand, in France. The objective of the breeding program was to identify new *Hydrangea* varieties with unique qualities for ornamental purposes. The crossing resulting in the new variety conducted by the inventors at a research nursery in Angers, France during 2007. Selection of the new variety was made during 2010.

The seed parent is an unpatented, unnamed proprietary variety *Hydrangea scandens*. The pollen parent is an unpatented, unnamed proprietary variety *Hydrangea* hybrid.

Asexual reproduction of the new cultivar 'FRENCH BOLERO' by softwood cuttings was first performed during the Summer of 2017 at a commercial greenhouse in Brain sur l'Authion, France. Subsequent propagation has shown that the unique features of this cultivar are stable and reproduced true to type in two successive generations.

SUMMARY OF THE INVENTION

The cultivar 'FRENCH BOLERO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FRENCH BOLERO'. These characteristics in combination distinguish 'FRENCH BOLERO' as a new and distinct *Hydrangea* cultivar:

1. Small, narrow leaves.
2. Large flattened inflorescences composed of light pink flowers.
3. Thin and numerous stems, easily branching.
4. Early flowering at each node.
5. Interspecific sterile hybrid.

PARENT COMPARISON

Plants of the new cultivar 'FRENCH BOLERO' are similar to plants of the seed parent in most horticultural characteristics, however, plants of the new cultivar 'FRENCH BOLERO' differ in the following:

1. Flowers of the new variety are large and light pink, flowers of the seed parent are small and white.

Plants of the new cultivar 'FRENCH BOLERO' are similar to plants of the pollen parent in most horticultural characteristics, however, plants of the new cultivar 'FRENCH BOLERO' differ in the following:

1. Inflorescence of the new variety are entirely sterile, inflorescence of the pollen parent include both sterile and fertile flowers.
2. Flowers of the pollen parent are darker pink than those of the new variety.
3. Stems of the new variety are thinner than stems of the pollen parent.

COMMERCIAL COMPARISON

'FRENCH BOLERO' can be compared to the commercial variety *Hydrangea* 'Runaway Bride', patent status unknown. These varieties are similar in most horticultural characteristics; however, 'FRENCH BOLERO' differs in the following:

1. 'French Bolero' has light pink flowers, 'Runaway Bride' has white flowers.

BRIEF DESCRIPTION OF THE PHOTOGRAPHS

Figure 1:
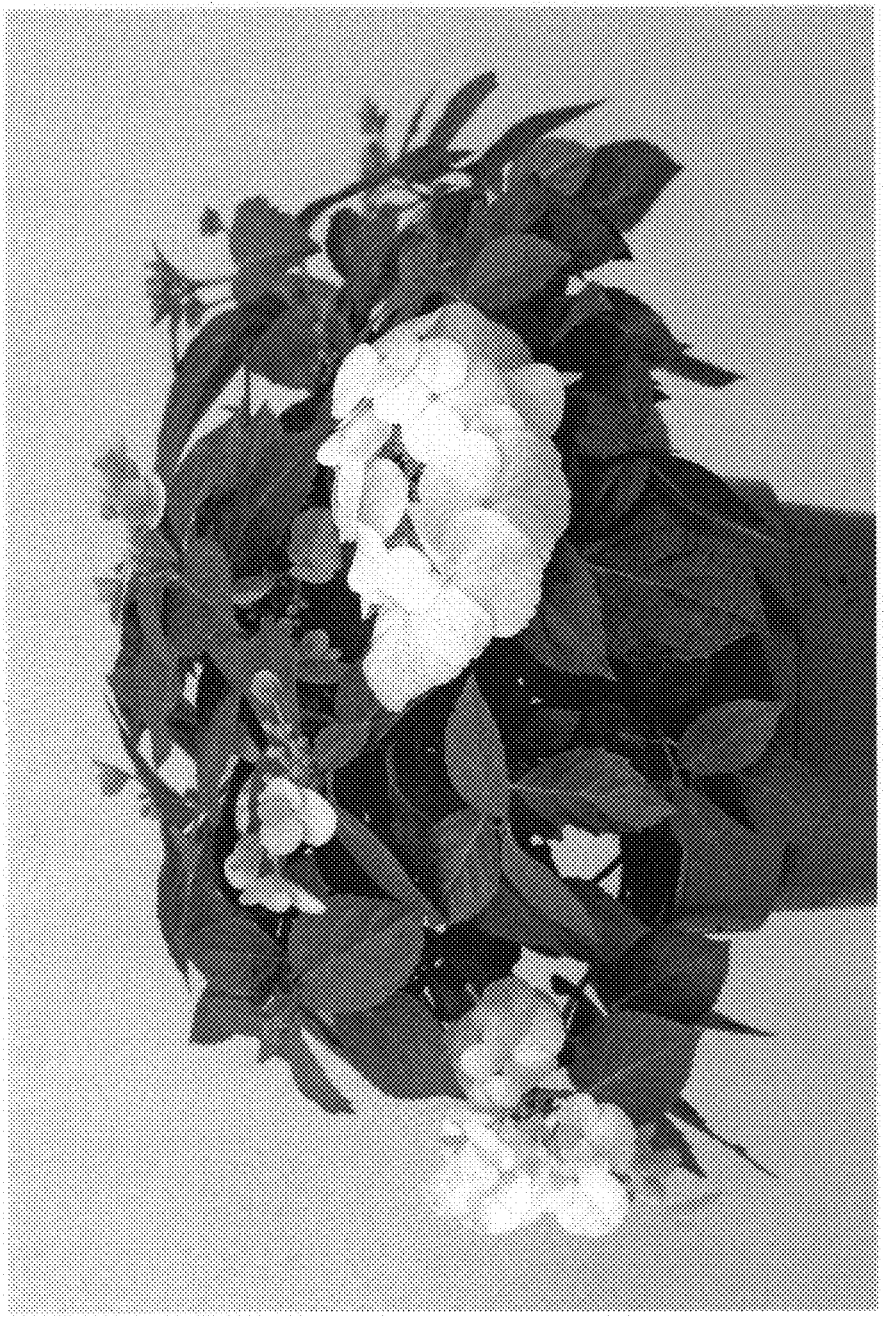

The accompanying photograph in FIG. 1 illustrates in full color a typical flowering plant of 'FRENCH BOLERO' grown in a greenhouse in France. Age of the plant photographed is approximately 1 year.

Figure 2:
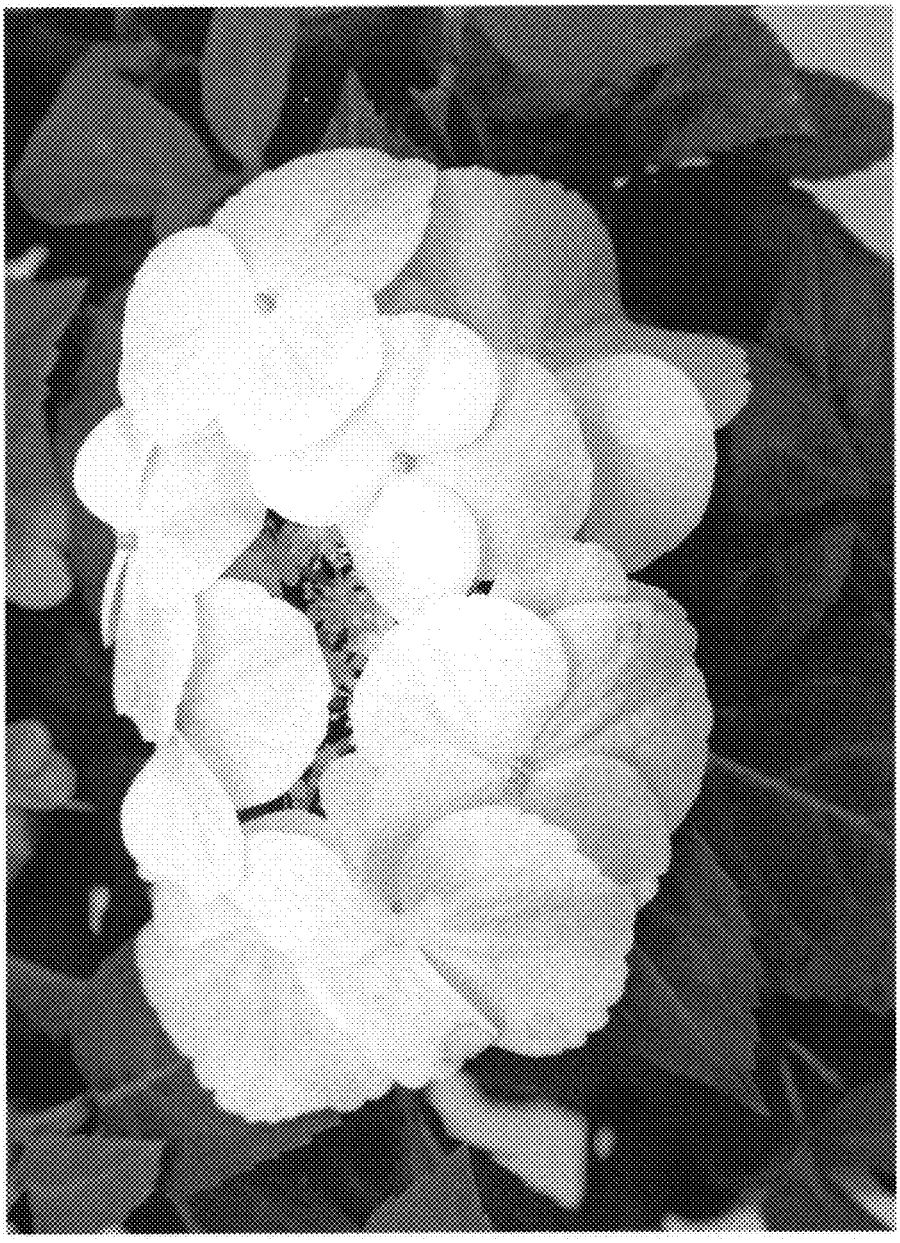

FIG. 2 illustrates a close up of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The 2015 Royal Horticultural Society Colour Chart except where general terms of ordinary dictionary significance are used. The following observations and measurements describe 'FRENCH BOLERO' plants grown in a greenhouse, in the Netherlands. The growing temperature ranged from approximately 18° C. to 27° C. daytime and 5° to 10° C. at night. Measurements and numerical values represent averages of typical plant types. Measurements were taken during July of 2017.

Botanical classification: *Hydrangea* hybrid 'FRENCH BOLERO'.

PROPAGATION

Time to initiate roots: Approximately 16 to 28 days at approximately 22 to 27° C.

Root description: Thick and fine, freely root branching and dense, fibrous. White to tan, not accurately measured with the R.H.S. chart.

Propagation method: Softwood cuttings.

PLANT

Age of plant described: 2 years.

Pot size: 13 cm.

Growth habit: Broad spreading-upright.

Overall plant shape: Flattened globular.

Height: Average: 19.5 cm.

Plant spread: 39.3 cm.

Growth rate: Moderate.

Plant vigor: Moderate to high.

Branching characteristics: Very free branching. Pinching not required but will improve branching.

Length of lateral branches/stems: Average: 9.9 cm (excluding inflorescence).

Number of lateral branches: Average 28.

Diameter of lateral branches: Average: 0.3 cm.

Lateral branch shape and appearance: Round.

lateral branch strength: Strong.

Internode length: Average: 2.4 cm.

Branch/stem color:

*Immature*.—RHS Yellow-Green 144A.

*Mature*.—RHS Yellow-Green 146C.

*Older bark*.—RHS Brown 200C and 200D.

Branch/stem texture: Rounded, glabrous.

Branch angle: Upright, in average angle of 55° to soil level (=0°), varying between 20° and 90°.

Branch pubescence: No.

FOLIAGE

Leaf:

*Arrangement*.—Opposite.

*Average length*.—7.1 cm.

*Average width*.—4.5 cm.

*Shape of blade*.—Ovate or narrow ovate.

*Apex*.—Apiculate.

*Base*.—Very short acute to near obtuse.

*Margin*.—Serrate.

*Texture and appearance of top surface*.—Smooth, very slightly rugose.

*Texture and appearance of bottom surface*.—Smooth, slightly rugose.

*Color*.—Solid, non-variegated. Young foliage upper side: RHS Green 137B. Young foliage under side: RHS Yellow-Green 146B. Mature foliage upper side: Green to Yellow-Green; in between RHS NN137A and 147B but slightly darker. Mature foliage under side: RHS Yellow-Green 147B.

*Venation*.—Type: Pinnate. Venation color upper side: RHS Yellow-Green 144B. Venation color under side: RHS Yellow-Green 146D.

Petiole:

*Average length*.—0.9 cm.

*Diameter*.—1.5 to 2 mm.

*Color*.—Upper side: RHS Yellow-Green 144B. Under side: RHS Yellow-Green 144B.

*Texture upper side*.—Smooth, moderately glossy.

*Texture under side*.—Smooth, moderately glossy.

FLOWER

Bloom period:

*Natural season*.—Late spring to late summer.

Inflorescence:

*Arrangement*.—Terminal corymb.

*Type*.—Lacecap.

*Shape*.—Flattened, fertile flowers surrounded by sterile flowers.

*Height*.—Average 5.2 cm.

*Diameter*.—Average 11.5 cm.

*Quantity of flowers per inflorescence*.—Fertile flowers: Average 57. Sterile Flowers: Average 13.

*Fragrance*.—None.

Fertile flower:

*Bud*.—Shape: Obovate. Length: Average: 0.4 cm. Diameter: Average: 0.25 cm. Color: RHS Yellow-Green 144B, base (immature sepals) Yellow-Green 146C.

*Flower*.—Aspect: Upright. Shape: Rotate, petals dropped when maturing. Diameter: Average: 0.7 cm. Depth: Average: 0.45 mm. Longevity: Average 5 days.

*Petal*.—Arrangement: Rotate. Persistent or self-cleaning: Self-cleaning. Petals per flower: Average 5, occasionally 6. Shape: Ovate, concave. Tip: Acute. Base: Cuneate. Margin: Entire. Length: Average 0.4 cm. Width: Average 0.25 cm. Texture, upper side: Glabrous, matte. Texture, under side: Glabrous, matte. Color when opening, upper side: RHS White N155C, fading to Yellow-Green 145C towards the top. Color when opening, under side: RHS White N155D, fading to Yellow-Green 145C towards the top. Color fully opened, upper side: RHS White NN155D, fading to Yellow-Green 145C towards the top. Color fully opened, under side: RHS White NN155D, fading to Yellow-Green 145C towards the top. Color fading, upper side: Not fading but dropped when mature. Color fading, under side: Not fading but dropped when mature.

*Sepals*.—Sepals per flower: Average 5, occasionally 6. Arrangement: Rotate. Shape: Broad ovate. Tip: Acute. Base: Broad cuneate. Margin: Entire. Length: Average 0.15 cm. Width: Average 0.1 cm. Texture, upper side: Glabrous, matte. Texture, under side: Glabrous, matte. Color when opening, upper side: RHS White N155A, fading to Yellow-Green 145B towards the top. Color when opening, under side: RHS White N155A, fading to Yellow-Green 145B towards the top. Color fully opened, upper side: RHS White N155A, fading to Yellow-Green 145B/C towards the top. Color fully opened, under side: RHS White N155A, fading to Yellow-Green 145B/C towards the top. Color fading, upper side: Not fading. Color fading, under side: Not fading.

*Pedicel*.—Length: Average: 0.4 cm. Diameter: Average 0.75 mm. Angle: Average 20° (0°=vertical), varying between 0° and 35°. Strength: Moderate. Texture: Matte, sparsely covered with a thin pubescence; average length of hairs shorter than 0.2 mm, colored white, too small to be measured with R.H.S. color chart. Color: RHS Red-Purple 69B. Base of joint pedicels Greyed-Red 178B.

Sterile flower:

*Bud*.—Shape: Narrow cup-shaped. Length: 0.7 cm. Diameter: Average: 0.5 cm. Color: RHS Yellow-Green 144B.

*Flower*.—Aspect: Upright to slightly outward. Shape: Rotate. Diameter: Average: 5.1 cm. Depth: Average: 0.9 cm. Longevity: Average 6 weeks.

*Petal*.—Arrangement: Rotate. Persistent or self-cleaning: Persistent. Petals per flower: Average 4. Shape: Ovate, strongly concave. Tip: Acute. Base: Cuneate. Margin: Entire. Length: Average 0.3 cm. Width: Average 0.2 cm. Texture, upper side: Glabrous, matte. Texture, under side: Glabrous, matte. Color when opening, upper side: RHS White N155C, fading to White 155C towards the top. Color when opening, under side: RHS White N155C, fading to White 155C towards the top. Color fully opened, upper side: RHS White N155C, fading to White 155C towards the top. Color fully opened, under side: RHS White N155C, fading to White 155C towards the top. Color fading, upper side: Not fading but dropped when mature. Color fading, under side: Not fading but dropped when mature.

*Sepals*.—Sepals per flower: Average: 4, occasionally 3 or 5. Arrangement: Rotate/cruciform, overlapping. Shape: Reniform. Tip: Obtuse, larger sepal occasionally shallow emarginate. Base: Broad cuneate. Margin: Upper half serrate-crenate. Length: Shorter sepal average: 2.0 cm. Longer sepal average: 2.7 cm. Other sepals average: 2.4 cm. Width: Shorter sepal average: 2.0 cm. Longer sepal average: 2.7 cm. Other sepals average: 3.8 cm. Texture, upper side: Glabrous, matte. Texture, under side: Glabrous, matte. Color when opening, upper side: RHS Red-Purple 69B, fading to White N155B towards the base, veined Red-Purple 69A. Color when opening, under side: RHS Red-Purple 69C, fading to White N155B towards the base. Color fully opened, upper side: RHS Red-purple 69A, fading to Red-Purple 65C towards the base, veined Red-Purple 65B. Color fully opened, under side: RHS Red-Purple 65D. Color fading, upper side: Not fading. Color fading, under side: Not fading.

*Pedicel*.—Length: Average: 1.9 cm. Diameter: Average 0.1 cm. Angle: Average 20° (main peduncle 0°), varying between 20° and 30°. Strength: Moderately strong. Texture: Matte, moderately covered with a thin pubescence; average length of hairs shorter than 0.2 mm, colored white, too small to be measured with R.H.S. color chart. Color: RHS White N155B, fading to Red-Purple 69C towards distal end. Base of joint pedicels Greyed-Red 178B.

REPRODUCTIVE ORGANS

Fertile flower:

*Stamen*.—Number: Average 10. Filament length: Average 0.3 cm. Filament color: RHS White NN155D, slightly tinged Red-Purple 69D. Anther shape: Broad oblong. Anther length: Average 0.8 mm. Anther color: RHS Yellow-White 158C. Pollen amount: Low to moderate. Pollen color: RHS Greyed-Yellow 160D.

*Pistil*.—Number: Average 3. Length: Average 0.2 cm. Stigma shape: Club-shaped. Stigma color: RHS White NN155D. Style length: Average 0.15 cm. Style color: RHS White N155B. Ovary color: RHS White NN155D.

Sterile flower:

*Stamen*.—Number: Average 8. Filament length: Average 0.2 cm. Filament color: RHS White N155B, and lighter. Anther shape: Broad oblong. Anther length: Average 0.8 mm. Anther color: RHS Yellow-White 158C. Pollen amount: Low to moderate. Pollen color: RHS Greyed-Yellow 160D.

*Pistil*.—Number: Average 3. Length: Average 0.1 cm. Stigma shape: Club-shaped. Stigma color: RHS White NN155D. Style length: Average 0.5 mm. Style color: RHS White N155B. Ovary color: RHS White NN155D.

OTHER CHARACTERISTICS

Disease resistance: Neither resistance nor susceptibility to diseases or pests of *Hydrangea* has been observed in this variety.

Cold tolerance: −24° C. to 38° C.

Fruit/seed production: Not observed to date.

What is claimed is:

1. A new and distinct cultivar of *Hydrangea* plant named 'FRENCH BOLERO' as herein illustrated and described.

* * * * *